United States Patent [19]

Konrad et al.

[11] 4,396,392

[45] Aug. 2, 1983

[54] METHOD FOR THE COLORING OF HAIR

[75] Inventors: Eugen Konrad, Darmstadt, Fed. Rep. of Germany; Herbert Mager, Fribourg, Switzerland

[73] Assignee: Wella AG, Darmstadt, Fed. Rep. of Germany

[21] Appl. No.: 127,507

[22] PCT Filed: Jul. 25, 1979

[86] PCT No.: PCT/EP79/00058
§ 371 Date: Mar. 5, 1980
§ 102(e) Date: Mar. 5, 1980

[87] PCT Pub. No.: WO80/00303
PCT Pub. Date: Mar. 6, 1980

[30] Foreign Application Priority Data

Aug. 3, 1978 [DE] Fed. Rep. of Germany ....... 2833989

[51] Int. Cl.$^3$ .............................................. A61K 7/13
[52] U.S. Cl. .......................................... 8/412; 8/406; 8/408; 8/421
[58] Field of Search ................... 8/412, 421, 408, 406; 564/439

[56] References Cited

FOREIGN PATENT DOCUMENTS 2501862 7/1975 Fed. Rep. of Germany .......... 8/412

OTHER PUBLICATIONS

Chemical Abstracts, p. 3605 of Dec. Index, vols. 11–20, vol. 15: 3498[3], vol. 16: 1429[1], vol. 19: 1413[2].
Davidson, "Intermediates for Dyestuffs", published by Ernest Benn Limited, London, (1926), p. 85.

*Primary Examiner*—Albert T. Meyers
*Assistant Examiner*—John M. Kilcoyne
*Attorney, Agent, or Firm*—Michael J. Striker

[57] ABSTRACT

Agents for the oxidative dyeing of hair, containing as coloring component 6-amino-3-methylphenol, also in the form of its salts or phenolates. The coloring component is contained in these agents in a quantity of about 0.01 to 2.0 percent by weight, alone or in a mixture with the customary developing and coupling substances. In the case of a mixture, the 6-amino-3-methylphenol is preferably used at a molar ratio below normal relative to these developing and coupling substances. The oxidative reaction of the 6-amino-3-methylphenol proceeding with an intensive yellow coloring is generally not influenced by the customary developing and coupling substances that may be present.

4 Claims, No Drawings

METHOD FOR THE COLORING OF HAIR

The object of the invention are agents for the oxidative coloring of hair, characterized by containing 6-amino-3-methylphenol as coloring component.

Coloring agents on the basis of oxidative colorants resulting from oxidative coupling of certain developing substances with certain coupling substances have obtained essential importance in the dyeing of hair. 2,5-diamino toluene, p-amino phenol and 1,4 diamino benzene are used in particular as developing substances. Resorcin, 4-chlororesorcin, —naphtol, m-aminophenol and derivatives of m-phenylene diamine such as m-toluylene diamine and 2,4-diaminoanisole are considered as preferentially used coupling substances. Apart from these initial dyeing stages, importance as constituents of oxidative hair-coloring agents is furthermore to be given to colorants directly drawing onto the hair, particularly direct-drawing aromatic nitro colorants. Dyeing in yellow, orange, red and violet can be obtained with these direct-drawing colorants.

Colorants used in the dyeing of human hair must satisfy numerous demands. They must be unobjectionable as to toxicology and dermatology, and enable dyeing to the desired intensity. It is furthermore required that a wide range of different tints must be obtainable by the combination of suitable initial coloring stages and suitable direct colorants. Furthermore, the resulting coloring should, to a good degree, be fast to light and resistant to permanent wave treatment, acids, and rubbing. Such colorings must, at any rate, remain stable against the influence of light, rubbing, and chemical agents, for a period of at least 4–6 weeks.

Due to the multitude of requirements, the initial coloring stages and direct-drawing colorants as used at present cannot give full satisfaction.

Direct-drawing aromatic nitro colorants will furthermore produce irregularities in coloring when used on hair that has been damaged to different degrees. In many instances, a sufficiently intensive coloring of porous, chemically damaged, hair tips is thus not possible.

Application of o-aminophenol in oxidative hair dyeing agents is merely possible to a limited extent, due to the only slight coloring intensity achieved with this substance.

Contrary to the above, it has now been found that agents for the oxidative dyeing of hair, containing 6-amino-3-methylphenol and/or its salts with inorganic or organic acids, or containing, respectively, the phenolates formed by this phenol derivative with an alkaline solution will satisfy the aforenamed requirements to a very large degree.

The hair dyeing agents as per invention may contain the 6-amino-3-methylphenol and/or its salts or phenolates respectively, alone or also as a mixture with the developing and coupling substances usual in hair coloring. If a mixture is present, the 6-amino-3-methylphenol will be applied in a molar ratio below normal relative to these developing and coupling substances. In particular instances however, an equimolar ratio or a respective excess ratio may be found suitable.

The hair dyeing agents as per invention should contain 0.01 to 2.0 percent by weight, preferably 0.02 to 0.3 percent by weight of 6-amino-3-methylphenol.

As usual developing substances, that may be obtained in the dyeing agents as per invention, 1,4-diamino benzene 2,5-diamino toluene and p-aminophenol should be named in particular.

Among the usual coupling substances, α-naphtol, 3,4 diaminobenzoic acid, resorcin, 4-chlororesorcin, m-aminophenol, m-phenylenediamine, m-toluylene diamine, 2,4-diamine anisole, 2,4-diaminobenzyl alcohol and 3-amino-6-methylphenol or mixtures thereof may be taken into consideration as constituents of customary hair dyeing preparations.

To obtain certain coloring nuances, customary direct-drawing colorants for instance triphenylmethane colorants such as Diamond Fuchsin (C.I. 42 510) and Leather Ruby HF (C.I. 42 520), aromatic nitro colorants such as 2-nitro-1,4-diamino benzene, azo dyes such as Acid Brown 4 (C.I. 14 805) and Acid Blue 135 (C.I. 13 385), anthraquinone dyes such as Disperse Violet 4 (C.I. 61 105), Disperse Blue 1 (C.I. 64 500) Disperse Red 15 (C.I. 60 710) Disperse Violet 1 (C.I. 61 100), and furthermore 1, 4, 5, 8-tetra amino anthraquinone and 1,4-diamino-anthraquinone may also be contained.

The form in which the hair dyeing agents as per invention are prepared, may be a solution, a cream, a gel or an emulsion. Its composition will represent a mixture of the coloring components with the usual constituents of such preparations. Usual constituents of creams, emulsions or gels are considered to be, for instance, wetting agents or emulsifiers from the classes of anionic or noniogenic surfactants such as sulfates of fatty alcohols, alkanolamides of fatty alcohols, alkyl sulfonates, alkylbenzene sulfonates, ethoxylated fatty alcohols, ethoxylated nonylphenols, and, furthermore, thickeners such as higher fatty alcohols, starch, cellulose derivatives, paraffin oil and fatty acids, as well as conserving agents such as lanolin derivatives, cholesterol and pantothenic acid.

The aforenoted constituents are used in quantities customary for such purposes, the wetting agents and emulgators for instance, in concentrations of about 0.5 to 30 percent by weight, whilst the thickeners may be contained in the preparations in quantities of about 0.1 to 25 percent by weight.

The hair dyeing agents may furthermore contain other customary additives, for instance antioxydants such as ascorbic acid or alkaline sulfite, perfume oils, lower aliphatic alcohols such as ethanol or isopropanol, alkaline hydroxides, complex formers and others.

The dyeing agents as per the present application are adjusted to a pH value within the weakly acidic, neutral or alkaline range, this irrespective of the form of their preparation. They have, in particular, a pH value between 8.0 and 11.5 within the alkaline range, adjustment being preferably made with ammonia. This may, however, also be accomplished by using organic amines, e.g. monoethanolamine or triethanolamine.

The 6-amino-3-methylphenol as essential constituent of the hair dyeing agent as per invention will, when affected by a suitable oxidizing agent, result in extremely intensive yellow colorations of the hair. A reaction of the aforenoted substance with itself appears to be the basis for these colorations.

The above oxidative colorant can, as already noted, be used in a mixture with customary developing and coupling components, wherein however, under the oxidative conditions of hair dyeing it will not react with these components. The chemical reactions between the developing and coupling substances as present, will therefore, in general, proceed without being influenced by the 6-amino-3-methylphenol contained in the hair dyeing agents as per invention. On the other hand, the chemical reaction of this phenol derivative with itself, proceeding with a concomitant yellow coloration, will, in general, not be influenced by the usual developing and coupling components as contained therein. A similarity with colorations on the basis of direct-drawing aromatic nitro-colorants exists here in respect of this independence and parallelism of the dyeing sequence based upon 6-amino-3-methylphenol.

Using 6-amino-3-methylphenol as constituent of the hair dyeing agent as per invention, makes it possible to replace the direct-drawing yellow and orange coloring aromatic nitro colorants which have disadvantageous properties, and at the same time to improve the dyeing characteristics. By this, it will then also become possible to intensively color porous, chemically damaged, hair tips.

Use of 6-amino-3-methylphenol also represents an essential advance in respect of toxicology and dermatology, as can be seen, for instance, when using it in place of the customary 4-nitro-1,2 diaminobenzene. The latter nitro compound acts as sensitizer and is furthermore of a relatively high acute toxicity, whilst the phenol derivative as per the present invention, does not show these disadvantages. Beyond this, the high coloring strength of the 6-amino-3-methylphenol will allow using the substance in the hair dyeing agents as per invention in a very low concentration.

Use of the hair dyeing agents as per the present application is made in the known manner, by mixing these with an oxidating agent shortly before use, and applying the mixture onto the hair. It is hydrogen peroxide in particular, for instance as a 6% solution, which is used to develop the hair coloring, or, respectively, its adductive compounds with urea, melamin or sodium borate.

The application temperatures are in the range of 15° to 50° C. After an application time of about 15 to 50 minutes, preferably about 30 minutes, the hair is rinsed with water and dried. In given instances, washing with shampoo is made after this rinse and a final rinse made with a weak organic acid such as, for instance, citric acid or tartaric acid.

As a constituent of the hair dyeing agents as per invention, the 6-amino-3-methylphenol is particularly suitable as colorant for producing nuances to obtain natural tints, color tints in fashion, and dull color nuances in particular. It is furthermore of importance in this context, that the yellow tints obtained by the 6-amino-3-methylphenol will undergo a variation in color towards orange if isomeric 6-methyl-3-aminophenol is present at the same time.

The following embodiments will more closely explain the object of the invention:

| Embodiment 1 | Hair dyeing solution |
|---|---|
| 0.3 g | 6-amino-3-methylphenol |
| 10.0 g | Di-glycolether sulfate of lauryl alcohol, 28% aqueous solution |
| 10.0 g | Isopropanol |
| 0.1 g | Sodium hydroxide, solid |
| 0.3 g | Sodium sulfite, anhydrous |
| 10.0 g | Ammonia, 22% |
| 69.3 g | Water |
| 100.0 g | |

50 g of the above hair dyeing agent are mixed with 50 ml hydrogen peroxide solution (6%) shortly before use. Subsequently, the mixture is applied onto the blond natural hair and allowed to act for 30 minutes at 40° C. The hair has obtained a bright yellow tint in full color.

| Embodiment 2 | Hair dyeing agent as a gel |
|---|---|
| 0.3 g | 6-amino-3-methylphenol |
| 0.2 g | 1,4-Diaminobenzene |
| 15.0 g | Oleic acid |
| 7.0 g | Isopropanol |
| 0.1 g | Sodium hydroxide, solid |
| 0.3 g | Ascorbic acid |
| 10.0 g | Ammonia, 22% |
| 67.1 g | Water |
| 100.0 g | |

50 g of the above hair dyeing agent are mixed with 50 ml hydrogen peroxide solution (6%) shortly before use, and the mixture subsequently applied onto light blond, partly greyed, natural hair. After an application time of 30 minutes at 40° C., rinsing with water and drying are made. The hair has obtained a uniform, blond, natural, color tint.

| Embodiment 3 | Hair dyeing agent as cream |
|---|---|
| 0.25 g | 6-amino-3-methylphenol |
| 0.30 g | 3-amino-6-methylphenol |
| 0.25 g | 1,4-Diaminobenzene |
| 3.50 g | Di-glycolether sulfate of lauryl alcohol, 28% aqueous solution |
| 15.00 g | Cetyl alcohol |
| 0.20 g | Sodium hydroxide, solid |
| 0.30 g | Sodium sulfite, anhydrous |
| 10.00 g | Ammonia, 22% |
| 70.40 g | Water |
| 100.00 g | |

Shortly before use, 50 g of this hair dyeing agent are mixed with 50 ml hydrogen peroxide solution (6%) and the mixture is allowed to act on blond, natural, hair for 30 minutes at 40° C. Rinsing with water is subsequently made and the hair dried. The hair is colored in an intensive, violet-shaded, red tint.

All percentages stated in the present application signify percent per weight.

We claim:

1. A method for dyeing human hair with oxidative dyes which comprises applying to said hair, at temperature of from 15° to 50° C. an effective amount for dyeing, of a mixture of a suitable oxidizing agent and an aqueous composition containing from 0.01 to 2.0% by weight of 6-amino-3-methyl-phenol, allowing said mixture to remain in contact with said hair for a period of time to effectively dye said hair, and thereafter rinsing said hair.

2. A method according to claim 1, wherein the mixture is allowed to remain in contact with the hair for a period of time in the range of 15 to 50 minutes.

3. A method according to claim 1, wherein the aqueous composition additionally comprises at least one of 1,4-diamino-benzene, 2,5-diamino-toluene, p-aminophenol, α-naphthol, 3,4-diamino-benzoicacid, resorcinol, 4-chloro-resorcinol, m-aminophenol, m-phenylene diamine, m-toluylenediamine, 2,4-diamino anisole, 2,4-diamino-benzylalcohol or 3-amino-6-methyl-phenol.

4. A method according to claim 1, wherein the aqueous composition additionally comprises at least one of Diamond Fuchsin (C.I. 42 510), Leather Ruby HF (C.I. 42 520), 2-nitro-1,4-diaminobenzene, Acid Brown (C.I. 14 805), Acid Blue 135 (C.I. 13 385), Disperse Violet 4 (C.I. 61 105), Disperse Blue 1 (C.I. 64 500), Disperse Red 15 (C.I. 60 710), Disperse Violet 1 (C.I. 61 100), 1,4,5,8-tetraamino-anthraquinone or 1,4-diamino anthraquinone.

* * * * *